(12) United States Patent
Stolting et al.

(10) Patent No.: US 7,608,720 B2
(45) Date of Patent: Oct. 27, 2009

(54) PROCESS FOR THE PREPARATION ON 2-AMINOMETHYLPYRIDINE DERIVATIVES

(75) Inventors: Jorn Stolting, Cologne (DE); Brian Burton, Cambridge (GB)

(73) Assignee: Bayer Cropscience AG (DE)

( * ) Notice: Subject to any disclaimer, the term of this patent is extended or adjusted under 35 U.S.C. 154(b) by 490 days.

(21) Appl. No.: 10/554,880

(22) PCT Filed: Apr. 26, 2004

(86) PCT No.: PCT/EP2004/006075

§ 371 (c)(1),
(2), (4) Date: Oct. 28, 2005

(87) PCT Pub. No.: WO2004/096772

PCT Pub. Date: Nov. 11, 2004

(65) Prior Publication Data

US 2006/0235229 A1    Oct. 19, 2006

(30) Foreign Application Priority Data

Apr. 28, 2003  (GB) .................................. 0309631.0

(51) Int. Cl.
*C07D 213/62* (2006.01)
*C07D 211/70* (2006.01)
(52) U.S. Cl. .................. 546/300; 546/315; 546/334
(58) Field of Classification Search .................. 546/329, 546/334, 300, 315
See application file for complete search history.

(56) References Cited

U.S. PATENT DOCUMENTS

| 4,889,721 A | 12/1989 | Ueda et al. .................. 424/448 |
| 5,105,011 A | 4/1992 | Grosselin et al. ............. 564/417 |
| 7,321,043 B2 * | 1/2008 | Dann et al. .................. 546/288 |

FOREIGN PATENT DOCUMENTS

| WO | WO 02/16322 | 2/2002 |
| WO | WO 02/055476 | 7/2002 |

OTHER PUBLICATIONS

Bystryakova, I.D.; Smirnova, N.M.; Safonova T.S., "Pyrido '2,3-d'dipyrimidines 8. Synthesis of Pyrrolo (2', 3': 4,5)pyrido'2,3-d'pyrimidines", *Chemistry of Heterocyclic Compounds (A Translation of Khimiya Geterotsiklicheskikh Soedinenii)*, 1993, pp. 687-690, XP009036531.

Vogl E.M.; Buchwald S.L.: "Palladium-Catalysed Monoarylation of Nitroalkanes", *Journal of Organic Chemistry*, 2002, vol. 67, pp. 106-111, XP002296541.

Feuer H; Lawrence J.P.: "Alkyl Nitrate Nitration of Active Methylene Compounds. IX The Nitration of Alkyl Substituted Heterocyclic Compounds", *Journal of Organic Chemistry*, 1972, vol. 37, No. 23, pp. 3662-3670, XP002296542.

Reid, J.G.; Reny Runge, J.M.: "Addition of Nitroalkanes to ortho-halo-nitrobenzenes. A new synthesis of 4-Chloro-7-(Trifluoromethyl)quinoline" *Tetrahedron Letters*, 1990, vol. 31, No. 8, pp. 1093-1096, XP002296544.

International Search Report dated Sep. 30, 2004.

Akio Kamimura et al.: "Diastereoselective Preparation of Anti-β-Amino Alcohols via Michael Addition of Alkoxide Anions to Nitroolefins and Subsequent Hydrogenation Reaction", *Tetrahedron Letters*, vol. 30, No. 6, pp. 731-734 (1989).

Srinivasan Nagarajan et al.: "Chemistry of Naturally Occurring Polyamines. Nonmetabolizable Derivatives of Spermine and Spermidine", *J. Org. Chem.*, 1986, vol. 51, No. 25, pp. 4856-4861.

R.F. Cunico: "Diazotative Deaminosilylation of β-Amino Silanesm", *J. Org. Chem.*, 1990, 55, 4474-4478.

*Organic Syntheses Coll.*, 1943, 2, p. 617-18.

William E. Parham et al.: "β-Nitrosulfides and β-Aminosulfides", *J. Am. Chem. Soc.*, 1951, vol. 73, pp. 1293-1295.

P.N. Rylander, *Hydrogenation Methods* (Best Synthetic Series, published by Academic Press) (1985), p. 148-49.

* cited by examiner

*Primary Examiner*—Janet L Andres
*Assistant Examiner*—Binta M Robinson
(74) *Attorney, Agent, or Firm*—Ostrolenk Faber LLP

(57) ABSTRACT

The present invention relates to a novel process for the preparation of 2-amino-methylpyridine derivatives of the formula (I), comprising reacting in a first step 2-substituted pyridine derivatives of the formula (II), with a nitroalkane of the formula (III), in the presence of a base resulting in 2-nitromethylpyridine derivatives of the formula (IV) and hydrogenating these 2-nitromethylpyridine derivatives of the formula (IV) in a second step in the presence of a catalyst and in the presence of an acid, where in the formulae n, X, Y, $R^1$, $R^2$ and A are as defined in the description.

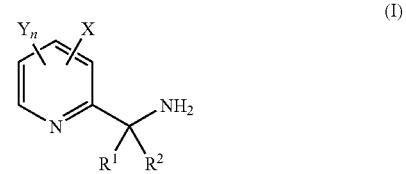

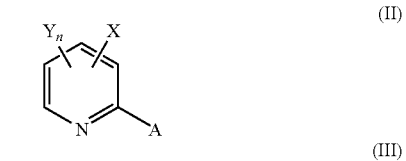

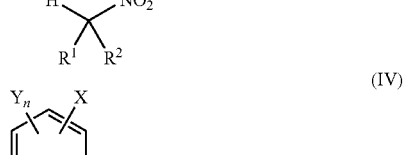

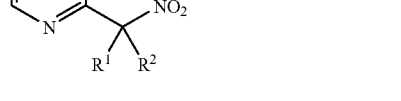

12 Claims, No Drawings

PROCESS FOR THE PREPARATION ON 2-AMINOMETHYLPYRIDINE DERIVATIVES

CROSS REFERENCE TO RELATED APPLICATION

The present application is a 35 U.S.C. § 371 national phase conversion of PCT/EP 2004/006075, filed April 26, 2004, which claims priority of GB Application No. 0309631.0 filed Apr. 28, 2003.

The present invention relates to a novel process for the preparation of 2-amino-methylpyridine derivatives which are useful as intermediates for the preparation of pesticides, by condensing a halogenopyridine derivative with nitromethane and subsequent catalytic hydrogenation of the resulting 2-nitromethylpyridine derivatives.

A condensation reaction of nitroethane with electron acceptor substituted halogenobenzene has been already disclosed (*Tetrahedron Lett.* 1990, 31, 1093-1096). The reduction of an aliphatic nitro group is a widely known reaction (cf. *J. Org. Chem.* 1993, 58, 2302: reduction with palladium/carbon and hydrogen in diethyl ether, cf. *Tetrahedron Lett.* 1989, 30, 731: reduction with Raney nickel and hydrogen, cf. *J. Org. Chem.* 1986, 51, 4856: reduction with sodium borohydride and catalytic nickel chloride hexahydrate, cf. *J. Org. Chem.* 1990, 55, 4474: reduction with lithium aluminium hydride, cf. *Org. Syn. Coll.* 1943, 2, 617: reduction with tin in hydrochloric acid, cf. *J. Am. Chem. Soc.* 1951, 73, 1293: reduction with iron in hydrochloric acid, cf. WO 02/055476: reduction with hydrogen or hydrogen-containing gas mixtures in the presence of a shaped Raney catalyst).

When the nitromethylpyridine is substituted by an additional halogen atom the difficulty exists to avoid the hydrogenolytic dehalogenation of the pyridine ring during the reduction step (P. N. Rylander, *Hydrogenation Methods*, Best Synthetic Series, Academic Press, 1985, page 148). Therefore, the above mentioned methods in general cannot be regarded to be applicable to halogen substituted nitromethylpyridine derivatives without significant further improvements.

We have now found a process to prepare 2-aminomethylpyridine derivatives which does not possess the above mentioned drawbacks, since only traces of dehalogenated product is observed, and which therefore is applicable to industrial scale process.

Accordingly, the present invention relates to a process for the preparation of 2-aminomethylpyridine derivatives of general formula (I) or a salts thereof

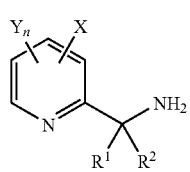

in which
n represents 0, 1, 2 or 3,
X represents a halogen atom,
Y represents a halogen atom, halogenoalkyl, alkoxycarbonyl or alkylsulphonyl, where Y may be identical or different, if n represents 2 or 3,
$R^1$ represents hydrogen, alkyl, cycloalkyl or cycloalkylmethyl,
$R^2$ represents hydrogen or alkyl,
$R^1$ and $R^2$ furthermore together represent alkylene, comprising reacting in a first step 2-substituted pyridine derivatives of the formula (II)

in which
n, X and Y are as defined above and
A represents a halogen atom, trifluoromethylsulphonyl or methylsulphonyl or any other radical which may act as a negatively charged leaving group,
with a nitroalkane of the formula (III)

in which
$R^1$ and $R^2$ are as defined above,
in the presence of a base
resulting in 2-nitromethylpyridine derivatives of the formula (IV)

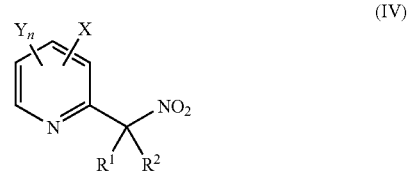

in which
n, X, Y, $R^1$ and $R^2$ are as defined above, and hydrogenating these 2-nitromethylpyridine derivatives of the formula (IV) in a second step in the presence of a catalyst and in the presence of an acid.

The formula (II) provides a general definition of the 2-substituted pyridine derivatives required as starting material for carrying out the first step of the process according to the invention.

Preferred definitions of the radicals of the 2-substituted pyridine derivatives of the formula (II) are given in the following.

n preferably represents 0, 1 or 2, particularly preferably represents 0 or 1, very particularly preferably represents 1.

X preferably represents fluorine, chlorine or bromine, particularly preferably represents fluorine or chlorine, very particularly preferably represents chlorine.

X preferably is located in the 3-position of the pyridine ring, i.e. in ortho position to the radical A.

Y preferably represents fluorine, chlorine, bromine, $C_1$-$C_6$-halogenoalkyl having 1 to 13 halogen atoms selected from the group consisting of fluorine, chlorine and bromine, ($C_1$-$C_6$-alkoxy)carbonyl or $C_1$-$C_6$-alkylsulphonyl, particularly preferably represents fluorine, chlorine, bromine, $C_1$-$C_4$-halogenoalkyl having 1 to 9 halogen atoms selected from the group consisting of fluorine, chlorine and bromine, ($C_1$-$C_4$-alkoxy)carbonyl or $C_1$-$C_4$-alkylsulphonyl, very particularly preferably represents chlorine, trifluoromethyl, trichloromethyl, methoxycarbonyl, ethoxycarbonyl, n-propoxycarbonyl, iso-propoxycarbonyl, methylsulphonyl or ethylsulphonyl.

Y preferably is located in the 5-position of the pyridine ring when n is 1, i.e. in para position to the radical A.

A preferably represents fluorine, chlorine, bromine, trifluoromethylsulphonyl or methylsulphonyl, or any other radical which may act as a negatively charged leaving group, particularly preferably represents chlorine, bromine or trifluoromethylsulphonyl, very particularly preferably represents chlorine.

Preferred starting material of the formula (II) are 2-substituted pyridine derivatives, in which n is 1, X is chlorine, Y is $C_1$-$C_4$-halogenoalkyl, in particular trifluoromethyl, and A is chlorine or trifluoromethylsulphonyl, in particular chlorine.

The particularly preferred 2-substituted pyridine derivative of formula (II) used as starting material for the process according to the invention is 2,3-dichloro-5-(trifluoromethyl)pyridine.

2-Substituted pyridine derivatives of the formula. (II) are known and/or can be prepared according to known methods.

The formula (III) provides a general definition of the nitroalkanes required as starting material for carrying out the first step of the process according to the invention.

Preferred definitions of the radicals of the nitroalkanes of the formula (III) are given in the following.

$R^1$ preferably represents hydrogen, $C_1$-$C_6$-alkyl, $C_3$-$C_8$-cycloalkyl or ($C_3$-$C_8$-cycloalkyl)methyl, particularly preferably represents hydrogen, $C_1$-$C_6$-alkyl, $C_3$-$C_6$-cycloalkyl or ($C_3$-$C_6$-cycloalkyl)methyl, very particularly preferably represents hydrogen, methyl, ethyl, n-propyl, iso-propyl, n-butyl, iso-butyl, sec-butyl, tert-butyl, n-pentyl, iso-pentyl, neo-pentyl, n-hexyl, iso-hexyl, neo-hexyl, cyclopropyl, cyclobutyl, cyclopentyl, cyclohexyl, cyclopropylmethyl, cyclobutylmethyl, cyclopentylmethyl or cyclohexylmethyl.

$R^2$ preferably represents hydrogen or $C_1$-$C_6$-alkyl, particularly preferably represents hydrogen, methyl, ethyl, n-propyl, iso-propyl, n-butyl, iso-butyl, sec-butyl, tert-butyl, n-pentyl, iso-pentyl, neo-pentyl, n-hexyl, iso-hexyl, neo-hexyl, very particularly preferably represents hydrogen, methyl, ethyl, n-propyl, iso-propyl, n-butyl, iso-butyl, tert-butyl, n-pentyl, iso-pentyl, n-hexyl or iso-hexyl.

$R^1$ and $R^2$ furthermore together preferably represent $C_2$-$C_5$-alkylene, particularly preferably represent —$(CH_2)_2$—, —$(CH_2)_3$—, —$(CH_2)_4$—, —$(CH_2)_5$—.

Nitroalkanes of the formula (III) are known chemical substances. Typical examples for nitroalkanes of the formula (III) are: nitromethane, nitroethane, 1-, 2-nitropropane, 2-nitropropane, 1-, 2-, 3-, 4-nitrobutane, 2-methyl-1-nitropropane, nitrocyclopropane, nitrocyclobutane, nitrocyclopentane, nitrocyclohexane, nitromethylcyclopropane. This list only exemplifies nitroalkanes of the formula (III) and does not limit the scope of the present invention.

The formula (IV) provides a general definition of the 2-nitromethylpyridine derivatives of the formula (IV) required as starting material for carrying out the second step of the process according to the invention.

The same preferred, particularly preferred and very particularly preferred definitions as given above for the formulae (II) and (III) apply for the radicals of the 2-nitromethylpyridine derivatives of the formula (IV).

2-Nitromethylpyridine derivatives of the formula (IV) are novel and also part of this invention.

Saturated or unsaturated hydrocarbon radicals, e.g. alkyl and alkenyl, can in each case be straight-chain or branched as far as this is possible, including in combination with heteroatoms, e.g. in alkoxy.

The process according to the present invention is particularly suitable for the preparation of 2-aminomethyl-3-chloro-5-trifluoromethylpyridine, by reaction of in the first step 2,3-dichloro-5-trifluoromethylpyridine with nitromethane in the presence of potassium tert-butanolate, sodium tert-butanolate, or potassium hydroxide in DMSO as diluent to give 3-chloro-2-nitromethyl-5-trifluoromethylpyridine, which in the second step is hydrogenated in hydrochloric acid using palladium on carbon as catalyst to yield 3-chloro-2-aminomethyl-5-trifluoromethylpyridine.

The first step of the process according to the present invention is carried out in the presence of a base. Suitable bases are in each case all inorganic and organic bases which are customary for such reactions. Preference is given to using alkaline earth metal or alkali metal alkoxides, such as sodium methanolate, sodium ethanolate, potassium tert-butanolate and sodium iso-butanolate, alkali metal and alkaline earth metal hydroxides, such as sodium hydroxide, calcium hydroxide or potassium hydroxide, alkali metal carbonates or hydrogencarbonates, such as sodium carbonate, potassium carbonate, lithium carbonate, caesium carbonate, potassium bicarbonate, sodium bicarbonate, and also tertiary amines, such as trimethylamine, triethylamine, tributylamine, diisopropylethylamine, N,N-dimethylaniline, pyridine, N-methylpiperidine, N,N-dimethylaminopyridine, diazabicyclooctane (DABCO), diazabicyclononene (DBN) or diazabicycloundecene (DBU). Particular preference is given to sodium methanolate, sodium ethanolate, potassium tert-butanolate, sodium tert-butanolate, sodium iso-butanolate, sodium hydroxide and potassium hydroxide, very particular potassium tert-butanolate, sodium tert-butanolate, sodium hydroxide and potassium hydroxide.

The first step of the process according to the present invention is optionally carried out in the presence of a diluent. Suitable diluents are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; alcohols, such as methanol, ethanol, tert- and iso-butanol; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; or sulphones, such as sulpholane.

The reaction temperatures employed to the first step of the reaction according to the invention may be varied over a broad range. In general the reaction is carried out between −20° C. and +150° C., preferably between 0° C. and 60° C., particularly preferably between 20° C. and 30° C.

The first step of the reaction is expediently carried out under atmospheric pressure, although it is also possible to work under reduced or elevated pressure. Particular preference is given to carrying out the reaction under atmospheric pressure.

The reaction time of the first step can be different depending on the scale of the reaction and may vary between 1 h and 48 h, preferably between 3 h and 24 h, particularly preferably between 5 h and 15 h.

The first step of the process is carried out in practice by reacting, for example, 1 mol of a 2-substituted pyridine derivative of formula (II) with between 1 and 10 mol, preferably between 1 and 5 mol, particularly preferably between 1 and 3 mol of the nitroalkane of the formula (III) in the presence of between 1 and 10 mol, preferably between 1 and 5 mol, particularly preferably between 1 and 3 mol of a base. In certain cases also other ratios may be applicable.

The second step of the process according to the invention is carried out in the presence of a catalyst. Suitable catalysts to be mentioned are Raney nickel, Raney cobalt, palladium on carbon, palladium salts, platinum and platinum oxides. Preference is given to Raney nickel, Raney cobalt and palladium on carbon. In particular palladium on carbon is used in a range of between 0.0001 to 2 equivalents of the 2-nitromethylpyridine derivative of the formula (IV). Ammonium chloride may be used as co-catalyst in a range of between 0 and 10 equivalents. To minimize dehalogenation, it might be beneficial to add a catalyst inhibitor (e.g. KBr) (cf. WO 02/16322)

The catalyst may be recycled according to methods well known by the man ordinary skilled in the art. Particularly, the catalyst may be easily recycled by filtration.

The second step of the process according to the present invention is carried out in the presence of an acid. Suitable acids are in each case all inorganic and organic acids which are customary for such reactions. Preference is given to using mineralic acids, such as hydrochloric, sulphuric and phoshoric acid; organic acids, such as formic, acetic, propionic, trifluoroacetic, trichloroacetic and methanesulphonic acid. Particularly hydrochloric or acetic acid are used.

The second step of the process according to the present invention is optionally carried out in the presence of a diluent. Suitable diluents are in each case all customary organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; alcohols, such as methanol, ethanol, tert- and iso-butanol; amides, such as N,N-dimethylformamide, N,N-dimethylacetamide, N-methylformanilide, N-methylpyrrolidone or hexamethylphosphoric triamide; esters, such as methyl acetate or ethyl acetate; organic acids such as acetic acid.

The reaction temperatures employed to the second step of the reaction according to the invention may be varied over a broad range. In general the reaction is carried out between −20° C. and +150° C., preferably between 0° C. and 60° C., particularly preferably between 20° C. and 30° C.

The second step of the reaction is carried out under a hydrogen pressure of between 0.5 and 200 bar, preferably of between 2 and 50 bar, particularly preferably of between 3 and 10 bar.

The reaction time of the second step can be different depending on the scale of the reaction and may vary between 1 h and 48 h, preferably between 3 h and 26 h.

The second step of the process is carried out in practice by hydrogenating, for example, 1 mol of a 2-nitromethylpyridine derivative of the formula (IV) in the presence of a catalyst and in the presence of an acid in an amount of between 0 and 10 mol, preferably between 1 and 5 mol, particularly preferably between 2 and 3 mol.

The process according to the present invention will now be illustrated with reference to the following example.

PREPARATION EXAMPLES

Example 1

(3-chloro-2-nitromethyl-5-trifluoromethylpyridine)

Potassium tert.-butanolate (20.2 g, 0.18 mol, 2 eq.) is placed together with 90 ml dry dimethyl sulphoxide in a 250 ml three-necked-bottle. Under dry argon atmosphere the nitromethane (11 g, 0.18 mol, 2 eq.) is added slowly with mechanical stirring while cooling with an ice bath. Stirring of the reaction mixture at 20° C. is continued for additional 15 min. Then 2,3-dichloro-5-trifluoromethylpyridine (19.44 g, 0.09 mol, 1 eq.) is added within 5 min at 17° C. The temperature first drops to 13° C., while at the end of the addition an exothermic reaction to 27° C. is observed. The mixture is allowed to cool to room temperature and stirring is continued for additional 14 h.

The dark brown crude product is poured into 150 ml of water, followed by three extractions with 50 ml ethyl acetate each. The combined organic layers are washed with three 30 ml portions of water and are subsequently dried over anhydrous sodium sulphate. After filtration the solvent is removed at 20° C. and under 150 mbar reduced pressure.

Yield: 22.8 g 3-chloro-2-nitromethyl-5-trifluoromethylpyridine (95.7% theoretical yield, 90.9% purity)

$^1$H NMR (d$_6$-DMSO): δ=6.21 (s, 2H), 8.68 (d, 1H), 9.05 (dd, 1H) ppm.

MS (LC/MS-coupling): m/z (%)=243 (36) and 241 (100) each [M$^+$+H].

Example 2

(3-chloro-2-nitromethyl-5-trifluoromethylpyridine PyMN)

Powdered potassium hydroxide (9.35 g, 0.15 mol, 3 eq.) is placed together with 70 ml dry DMSO in a 250 ml three-necked-bottom and under dry argon atmosphere the nitromethane (6.1 g, 0.1 mol, 2 eq) solved in 30 ml dry DMSO is added within 30 min slowly with mechanical stirring while cooling with an ice bath to maintain the temperature at 20° C. Stirring of the reaction mixture at 20° C. is continued for additional 15 min. Then 2,3-dichloro-5-trifluoromethylpyridine (10.80 g, 0.05 mol, 1 eq.) is added as one portion without endo- or exothermic reaction. The mixture is heated to 50° C., stirred for 3 h at this temperature and then allowed to cool to room temperature.

The dark brown crude product is poured into 500 ml of water, acidified by addition of diluted hydrochloric acid and followed by three extractions with 50 ml ethyl acetate each. The combined organic layers are washed with three 30 ml portions of water and are subsequently dried over anhydrous sodium sulphate. After filtration the solvent is removed at 20° C. and under 150 mbar reduced pressure.

Yield: 9.72 g 3-chloro-2-nitromethyl-5-trifluoromethylpyridine (73.9% theoretical yield, 91.4% purity)

Example 3

(3-chloro-2-aminomethyl-5-trifluoromethylpyridine hydrochloride)

A solution of 7.69 g (0.211 mol, 2 eq.) hydrogen chloride in dry methanol is prepared by dilution of 30% methanolic HCl with the appropriate amount of methanol. 3-chloro-2-nitromethyl-5-trifluoromethylpyridine (25.9 g, 0.106 mol, 1 eq.) and 5.50 g 5% Pd on carbon are placed together with the methanolic HCl obtained above in a hastelloy autoclave and the reduction is carried out under 5 bar hydrogen pressure for 26 h at room temperature.

After pressure regulation to 1 bar the catalyst is removed by filtration and after washing with small amounts of methanol all organic phases were combined and the solvent is removed at 30° C. and under 150 mbar reduced pressure.

The crude crystals obtained are suspended in dichloromethane for purification. After filtration and washing with dichloromethane the pale grey crystals are dried over phosphorous pentoxide.

Yield: 24.13 g 3-chloro-2-aminomethyl-5-trifluoromethylpyridine hydrochloride (92.5% theoretical yield, 99.9% purity $^1$H NMR (d$_6$-DMSO): δ=4.37 (d, 2H), 8.61 (d, 1H), 8.83 (s broad, 3H), 9.03 (d, 1H) ppm.

MS (GC/MS-coupling): m/z (%)=212 (13) and 210 (38) each [M$^+$], 184 (24) and 182 (79), 30 (100).

The invention claimed is:

1. A process for the preparation of 2-aminomethylpyridine derivatives of formula (I) or salts thereof

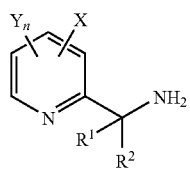
(I)

comprising the steps of reacting 2-substituted pyridine derivatives of the formula (II)

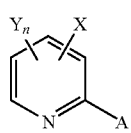
(II)

with a nitroalkane of the formula (III)

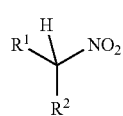
(III)

in the presence of a base resulting in 2-nitromethylpyridine derivatives of the formula (IV)

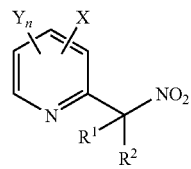
(IV)

and then hydrogenating these 2-nitromethylpyridine derivatives of the formula (IV) in the presence of a catalyst and an acid,
wherein
n represents 0, 1, 2 or 3,
X represents a halogen atom,
Y is selected from the group consisting of a halogen atom, halogenoalkyl, alkoxycarbonyl, and alkylsulfonyl, where each Y may be identical or different if n represents, 2 or 3,
R$^1$ is selected from the group consisting of hydrogen, alkyl, cycloalkyl, and cycloalkylmethyl,
R$^2$ is selected from the group consisting of hydrogen and alkyl, or
R$^1$ and R$^2$ taken together can represent alkylene, and
A is selected from the group consisting of halogen, trifluoromethylsulfonyl methylsulphonyl, and other radicals that can act as negatively charged leaving groups.

2. The process of claim 1, where the base is selected from the group consisting of sodium methanolate, sodium ethanolate, potassium tert-butanolate, sodium tert-butanolate, sodium iso-butanolate, sodium hydroxide, and potassium hydroxide.

3. The process of claim 1 wherein the catalyst is selected from the group consisting of Raney nickel, Raney cobalt, and palladium on carbon.

4. The process of claim 1 wherein the acid is selected from the group consisting of hydrochloric, sulphuric, phosphoric, formic, acetic, propionic, trifluoroacetic, trichloroacetic, and methanesulphonic acids.

5. The process of claim 1 wherein the 2-aminomethylpyridine derivative of formula (I) is 3-chloro-2-nitromethyl-5-trifluoromethylpyridine, the 2-substituted pyridine derivative of the formula (II) is 2,3-dichloro-5-trifluoromethylpyridine, the nitroalkane of the formula (III) is nitromethane, and the 2-nitromethylpyridine derivative of the formula (IV) is 3-chloro-2-nitromethyl-5-trifluoromethylpyridine.

6. The process of claim 5 wherein the base is selected from the group consisting of potassium tert-butanolate and potassium hydroxide.

7. The process of claim 5 wherein the acid is hydrogen chloride.

8. The process of claim 6 wherein the acid is hydrogen chloride.

9. The process of claim 5 wherein the catalyst is palladium on carbon.

10. The process of claim 6 wherein the catalyst is palladium on carbon.

11. The process of claim 7 wherein the catalyst is palladium on carbon.

12. The process of claim 8 wherein the catalyst is palladium on carbon.

* * * * *

UNITED STATES PATENT AND TRADEMARK OFFICE
CERTIFICATE OF CORRECTION

PATENT NO.         : 7,608,720 B2
APPLICATION NO.    : 10/554880
DATED              : October 27, 2009
INVENTOR(S)        : Stolting et al.

It is certified that error appears in the above-identified patent and that said Letters Patent is hereby corrected as shown below:

In the Title, Item (54) should read:

PROCESS FOR THE PREPARATION OF 2-AMINOMETHYLPYRIDINE DERIVATIVES

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,608,720 B2  Page 1 of 1
APPLICATION NO. : 10/554880
DATED : October 27, 2009
INVENTOR(S) : Stolting et al.

It is certified that error appears in the above-identified patent and that said Letters Patent is hereby corrected as shown below:

Title Page, Item (54) and at Column 1, lines 1 and 2, title should read:

PROCESS FOR THE PREPARATION OF 2-AMINOMETHYLPYRIDINE DERIVATIVES

This certificate supersedes the Certificate of Correction issued May 4, 2010.

Signed and Sealed this

First Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,608,720 B2  Page 1 of 1
APPLICATION NO. : 10/554880
DATED : October 27, 2009
INVENTOR(S) : Stolting et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 854 days.

Signed and Sealed this

Twelfth Day of October, 2010

David J. Kappos
*Director of the United States Patent and Trademark Office*